US012673141B2

(12) United States Patent
Yapici et al.

(10) Patent No.: US 12,673,141 B2
(45) Date of Patent: Jul. 7, 2026

(54) SYSTEM FOR SHAPE MEMORY ALLOY ENABLED DRUG RELEASE

(71) Applicant: OZYEGIN UNIVERSITESI, Istanbul (TR)

(72) Inventors: Guney Guven Yapici, Istanbul (TR); Gorkem Muttalip Simsek, Istanbul (TR)

(73) Assignee: OZYEGIN UNIVERSITESI, Istanbul (TR)

( * ) Notice: Subject to any disclaimer, the term of this patent is extended or adjusted under 35 U.S.C. 154(b) by 597 days.

(21) Appl. No.: 18/013,918

(22) PCT Filed: Dec. 31, 2020

(86) PCT No.: PCT/TR2020/051489
§ 371 (c)(1),
(2) Date: Dec. 30, 2022

(87) PCT Pub. No.: WO2022/146263
PCT Pub. Date: Jul. 7, 2022

(65) Prior Publication Data
US 2023/0293781 A1 Sep. 21, 2023

(51) Int. Cl.
*A61L 31/02* (2006.01)
*A61L 31/14* (2006.01)

(52) U.S. Cl.
CPC ........... *A61L 31/022* (2013.01); *A61L 31/145* (2013.01); *A61L 2300/606* (2013.01); *A61L 2400/16* (2013.01)

(58) Field of Classification Search
None
See application file for complete search history.

(56) References Cited

U.S. PATENT DOCUMENTS

2007/0282247 A1   12/2007   Desai et al.
2016/0015535 A1    1/2016   Charlebois et al.

FOREIGN PATENT DOCUMENTS

EP        0415671 A2    3/1991
EP        2279013 A2    2/2011
EP        2285429 A2    2/2011
WO     2007033282 A2    3/2007

OTHER PUBLICATIONS

Kalairaj, RSC Advances, 9, 59, 2019 (Year: 2019).*
Manivannan Sivaperuman Kalairaj, et al., Nitinol actuated soft structures towards transnasal drug delivery: a pilot cadaver study, Medical & Biological Engineering & Computing, 2020, pp. 611-623, vol. 58, No. 3.
Alessandra Maroni, et al., Retentive drug delivery systems based on shape memory materials, Journal of Applied Polymer Science, 2020, pp. 1-10, vol. 137, No. 25.
S. M. Pawde, et al., Characterization of Polyvinyl Alcohol/Gelatin Blend Hydrogel Films for Biomedical Applications, Journal of Applied Polymer Science, 2008, pp. 3431-3437, vol. 109.

* cited by examiner

*Primary Examiner* — Susan T Tran
*Assistant Examiner* — William Craigo
(74) *Attorney, Agent, or Firm* — Bayramoglu Law Offices LLC

(57) ABSTRACT

Disclosed is a drug delivery system that specifically carries and releases an active substance to a target organ or tissue. The coating of the shape memory component constituting the drug delivery system enhances the biocompatibility and controlled delivery of the active substance previously loaded into the coating material to the target organ or tissue.

7 Claims, 1 Drawing Sheet

SYSTEM FOR SHAPE MEMORY ALLOY ENABLED DRUG RELEASE

CROSS REFERENCE TO THE RELATED APPLICATIONS

This application is the national phase entry of International Application No. PCT/TR2020/051489 filed on Dec. 31, 2020, the entire contents of which are incorporated herein by reference.

TECHNICAL FIELD

The present invention relates to a system which is proposed for making the shape memory metal alloy more biocompatible and for using the same in active drug release.

BACKGROUND

Shape memory alloys (can also be abbreviated as SMA) are within a class of alloys that can return to its original shape without permanent deformation, by remembering the shape it has under certain temperature and mechanical loads or under a combination of these two conditions. The shape memory alloys can be used widely in many high-tech areas such as aviation, automotive, construction sites and sensors by means of these properties.

Shape memory alloys generally exhibit non-toxic biocompatibility properties when used in the body in addition to their shape memory properties. Shape memory alloys can also be used as a biomaterial in many biomedical applications such as stents, orthodontic wires, and orthopedic implants since they contain memory and biocompatibility properties together.

Shape memory alloys, which generally have high biocompatibility, exhibit tendency to ion release when it interacts with the human body which consists of mostly liquid and is a corrosive environment. As a consequence of this, undesirable damage mechanisms (inflammation, implant loosening, etc.) can be seen around the tissue surrounding the implant alloys. In such cases, for example nickel in Nickel-Titanium (Ni—Ti) alloys can be released into the body which limits the use of the material and the toxic effect of nickel can harm the body as well. It is required to enhance the biocompatibility properties of Ni—Ti alloys so as to eliminate such disadvantages.

Hydrogels are three-dimensional, porous materials composed of cross-linked polymers. They are widely used in tissue engineering and regional drug targeting due to their high water retaining capacity and non-toxic structures.

Hydrogels are divided into two as classical and sensitive to stimulus. The swelling balance of the stimulus sensitive, that is, smart hydrogels change rapidly with pH, temperature, electrical environment or other environmental stimuli. Smart hydrogels are classified as temperature sensitive, pH sensitive, sensitive to electrical stimulus according to their features.

In the state of the art, hydrogel-based drug delivery systems are used as oral, rectal, ocular, epidermal, and subcutaneous. These systems are formulated in many physical forms such as micro particles, nanoparticles, tablets, coatings and films.

Controlled release systems provide drug delivery wherein an active substance is designed in a manner such that it can be released from a system in a desired time, at a specified rate and in the required amount. When drugs are delivered into the body by a system that performs controlled release, the desired blood concentration is provided during the required period. Furthermore, systemic toxic effects seen in the conventional use are reduced. Control and maintenance of drug release kinetics is the key to successful application. The temperature-specific behaviors of the hydrogels sensitive to temperature are used to control drug release. Environment friendly hydrogels perform drug release with their reaction to external factors such as temperature, pH, enzyme, magnetic field, ionic strength, etc.

The invention numbered EP2285429 disclosed a polymer system to reduce the risk of late thrombosis relevant with the implantable medical devices.

The invention numbered EP2279013 generally relates to self-retaining systems for surgical procedures, methods of producing self-retaining systems for surgical procedures, and the usages thereof.

The invention numbered EP0415671 discloses a system for the release of an active substance in the stomach by directing and retarding the same.

As a result, a system that can eliminate the disadvantages of shape memory alloys during their use in various tasks in the body and that can enable them to take part in active drug release is considered to fulfill the novelty criterion for the relevant technical field.

SUMMARY

The present invention is related to a system comprising shape memory alloys to be used in vivo and used for active drug release while preventing the harmful effects such as toxic ion release. The system is recommended to eliminate the abovementioned disadvantages and to bring new advantages to the relevant technical field.

An object of the invention is to provide a system that allows enhancing the biocompatibility of shape memory alloys.

An object of the invention is to provide a system that enables shape memory alloys to take part in active drug release.

An object of the invention is to provide a system that enables the released active component to reach the required tissue.

DETAILED DESCRIPTION OF THE EMBODIMENTS

In this detailed description, the subject of the invention relates to a system proposed for making the subject matter shape memory alloy more biocompatible and for using the same in active drug release, is described by means of examples only for clarifying the subject matter such that no limiting effect is created.

In the drug release system proposed in the invention, Ni—Ti alloys are used as shape memory components. As known in the state of the art, Ni—Ti alloys are within a class of materials with high biocompatibility for human and animal bodies. However, as it is mentioned in the prior art, Ni—Ti alloys have the potential of releasing nickel ions leading to inappropriate conditions in the body. The proposed system aims to maximize the reliability of Ni—Ti alloys in terms of biocompatibility.

Figure 1:
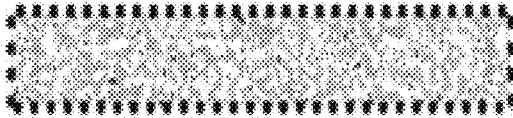
In FIG. 1, the representative view of the subject matter drug delivery system including the Ni—Ti wire coated hydrogel is shown.
Figure 2:
In FIG. 2, the plain view of the drug delivery system during its delivery to the target organ is given.

As shown in FIG. 1, the Ni—Ti alloy used in the invention is in the form of a thin and small wire. Said Ni—Ti alloy wire can be attached to the end portion of standard catheter tubes used in the art and can be transferred directly to the target area in the body. The size of the wire must be suitable for delivering with standard catheter systems.

The Ni—Ti alloy wire is coated with polyvinyl alcohol (to be abbreviated as PVA) hydrogel with a very thin coating in the system proposed in the invention. As known in the art, hydrogels can be used as a coating material in many systems.

PVA hydrogel, which has many advantages known in the art, is weak in terms of its mechanical properties. Therefore, it is not possible for hydrogels delivered directly to the body to remain in the body and to perform controlled release at the desired level. Both the biocompatibility of Ni—Ti alloys will enhance, and the weak mechanical properties of the hydrogels that are widely used in drug release will be eliminated with the hydrogel drug release system coated on Ni—Ti alloys. Furthermore, the features of hydrogels such as their porous structure, high liquid retaining capacity and non-toxicity make them a material that can be used frequently in drug release.

As known in the art, hydrogels can be loaded with effective chemical components and can take part in the controlled drug release to target organs.

The drug delivery system proposed in the invention is as follows;

a shape memory alloy wire that forms the main structure of the system and provides the specific movement of the target tissue or organ to which drug will be released and provides the active substance to release in a controlled manner and eventually reach the target organ or tissue by orienting at a certain angle after it reaches the vicinity of the target tissue or organ;

a hydrogel coated to encapsulate said shape memory alloy wire in such a way that it both acts as a coating to said shape memory alloy wire to prevent the release of toxic ions to the body and as well as carries the drug within its body;

and an active substance to be delivered to the relevant target organ or tissue.

Figure 3:
In FIG. 3, the view of the drug delivery system delivering the active substance to the target by bending at a certain angle, after it reaches the target organ, is given.

The shape memory alloy wire mentioned here is Ni—Ti alloy wire. The Ni—Ti wire mentioned in the invention is coated with a PVA hydrogel. Coated shape memory alloy wire is received into the body. The active substance on the hydrogel coating material of the shape memory alloy wire is delivered to the target organ while it is straight. When the hydrogel coated wire drug delivery system reaches the target organ or tissue as seen in FIG. 3, a controlled release is provided to the target by bending at a certain angle. Said bending angle is a value between 5° and 175°.

Ni—Ti wire will be transmitted to the desired area in the body with standard catheter systems. The diameter of the Ni—Ti wire is very thin and it will have a soft texture due to the hydrogel coating, thus there will not be any difficulty during its insertion into the body. The drug loaded hydrogel coated wire shall reach a certain temperature so as to obtain the desired angle. This heating is provided by applying an appropriate electrical current to the wire. The temperature level required for actuation in the form of bending will be adjusted to a level (generally <50° C.) so as to prevent possible damage to the surrounding tissue and epithelium.

The subject matter drug delivery system comprises the following process steps;

Shape setting and related preparations of the Ni—Ti wire,

Preparing the PVA hydrogel coating solution required for drug loading and coating the Ni—Ti wire with hydrogel, Loading an active substance appropriate for healing the diseased tissue or organ to the hydrogel coated Ni—Ti wire, Making the relevant characterizations for determining the drug release dynamics in relation to the actuation of the Ni—Ti wire.

Coating process performed on Ni—Ti wire mentioned in the invention is made by immersion. The coating solution used here is prepared by mixing gelatin and PVA materials and it is exposed to coating process by immersing Ni—Ti wires into the obtained solution. Ni release into the body is also prevented by coating the Ni—Ti wires with hydrogels. Another advantage of hydrogel is that it prevents any heat based tissue damage by means of its insulating features.

Transferring the obtained drug delivery system (hydrogel coated shape memory alloy wire) to the diseased tissue or organ comprises the following process steps;

placing the drug delivery system into the body through the standard catheters and forwarding the same to the target tissue or organ, heating the drug delivery system by applying electric current and actuating the same to bend at a predetermined angle, performing active substance release by squeezing the hydrogel coating in the drug delivery system as a consequence of bending, removing the drug delivery system out of the body by means of the catheter.

Cameras can be placed in standard catheters mentioned in the invention. This provides reaching the target tissue or organ in the body with ease and at higher accuracy.

Ni—Ti is heated with the application of electrical current, but possible damage to the tissue or organ is prevented by means of the hydrogel coating.

The active substance contained in the hydrogel can be released into the target tissue at various time intervals.

The novelty aspect of the invention, as stated previously, is based on a drug delivery system that specifically carries the active substance to the target organ or tissue. The invention relates to a system that provides specific access to damaged or diseased tissue or organ and subsequently provides controlled drug release.

The active substance to be used in the invention can be various. Any kind of active substance suitable for hydrogels with which controlled drug release can be performed, may be as follows; an analgesic or anti-inflammatory drug, protein or vitamin, nucleic acid, anticancer or an agent that can be used in tissue regeneration. Substances or agents in many different fields can be used as an active substance.

The drug delivery system proposed in the invention provides that the patient enters the healing process more quickly and the healthy cells are not affected by said treatment mechanisms, during the transport and controlled release of the active substance specific to the target tissue or organ.

What is claimed is:

1. A drug delivery system carrying an active substance for treating various diseases in a body, wherein said drug delivery system comprises:

a shape memory alloy wire forming a main structure of the drug delivery system, wherein the shape memory alloy wire provides a specific movement to a target tissue or a target organ, wherein a drug is configured to be released to the target tissue or the target organ, and the shape memory alloy wire provides release of an active substance in a controlled manner and orients at a certain angle after reaching a vicinity of the target tissue or the target organ;

a hydrogel coating to encapsulate said shape memory alloy wire, wherein the hydrogel acts as a coating to said shape memory alloy wire to prevent release of toxic ions to the body and a drug loaded hydrogel carries the drug within the body;

and the active substance to be delivered to the target organ or the target tissue;

wherein the drug delivery system is configured to be directed to the target organ or the target tissue and bends at an angle between 5° and 175° once the drug delivery system reaches the target organ or the target tissue to release the active substance by an actuation of the shape memory alloy wire via bending the hydrogel coating;

wherein said hydrogel coating is obtained from a mixture of gelatin and PVA materials;

and wherein the drug delivery system further comprises a catheter, the shape memory alloy wire being attached to a distal end portion of the catheter such that the hydrogel-coated wire is deliverable to and removable from the body by means of the catheter.

2. The drug delivery system according to claim 1, wherein said shape memory alloy wire is a Ni—Ti alloy.

3. The drug delivery system according to claim 1, wherein the hydrogel coating that encapsulates the shape memory alloy wire is formed by immersion coating, by immersing the wire into a solution comprising gelatin and PVA materials.

4. The drug delivery system according to claim 1, wherein the drug delivery system is configured to be used in types of cancer, for diseased tissues, in relief of various pains, in conditions where antiviral, antibacterial and antiparasitic drugs are required, and tissue regeneration is required, wherein the active substance is configured to be delivered with a hydrogel coated material.

5. The drug delivery system according to claim 1, wherein the active substance is comprised of analgesic or anti-inflammatory drugs suitable for hydrogels with controlled drug release, protein or vitamins, nucleic acids, anticancer or tissue regeneration agents, antiviral, antibacterial and anti-parasitic drugs.

6. A process of fabricating the drug delivery system according to claim 1, comprising the following process steps;

preparing a Ni—Ti wire by providing memory properties to the Ni—Ti wire, preparing a hydrogel coating solution required for drug loading and coating the Ni—Ti wire with the hydrogel, and loading the active substance for healing a diseased tissue or a diseased organ to a hydrogel coated Ni—Ti wire.

7. The process of fabricating the drug delivery system according to claim 6, wherein said hydrogel coating solution is obtained from a mixture of gelatin and PVA materials, and said hydrogel coating solution is applied on said Ni—Ti wire.

* * * * *